United States Patent [19]

Lin et al.

[11] 4,123,466

[45] Oct. 31, 1978

[54] PROCESS FOR NITRATING AROMATIC HYDROCARBONS

[75] Inventors: Chung-Yuan Lin, Northford; Fred A. Stuber, North Haven; Henri Ulrich, Northford, all of Conn.

[73] Assignee: The Upjohn Company, Kalamazoo, Mich.

[21] Appl. No.: 859,388

[22] Filed: Dec. 12, 1977

[51] Int. Cl.$^2$ .............................................. C07B 11/00
[52] U.S. Cl. .................................. 260/645; 260/688
[58] Field of Search ......................................... 260/645

[56] References Cited

U.S. PATENT DOCUMENTS

| | | | |
|---|---|---|---|
| 3,415,876 | 12/1968 | Boonstra et al. | 260/645 X |
| 3,922,315 | 11/1975 | Mitchell et al. | 260/645 |
| 4,028,425 | 6/1977 | Gilbert | 260/645 |

Primary Examiner—Leland A. Sebastian
Attorney, Agent, or Firm—Denis A. Firth; John Kekich

[57] ABSTRACT

An improved process for the nitration of aromatic hydrocarbons is described. The aromatic hydrocarbon (benzene, toluene of particular interest) is reacted with gaseous nitrogen dioxide in the presence of a catalytic amount of sulfuric acid and in the absence of oxygen. The process is highly selective and avoids the formation of undesired by-products. The acid employed as catalyst can be recovered and recycled after removal of water of condensation liberated in the reaction.

12 Claims, No Drawings

PROCESS FOR NITRATING AROMATIC HYDROCARBONS

BACKGROUND OF THE INVENTION

1. Field of the Invention

This invention relates to a process for the nitration of aromatic hydrocarbons and is more particularly concerned with an improved catalytic process for the selective nitration of aromatic hydrocarbons.

2. Description of the Prior Art

The nitration of aromatic hydrocarbons, and, in particular, of benzene and toluene, is normally carried out commercially by reacting the aromatic hydrocarbon with a mixture of nitric and sulfuric acids under controlled temperature; see, for example, Kirk-Othmer, Encyclopedia of Chemical Technology, 13, 836–7 and 844–6, 1967. Although many variations of this method have been investigated, it has not yet been possible to devise modifications or improvements which would avoid the use of large volumes of the highly corrosive mixture of nitric and sulfuric acids and also avoid the formation of by-products including the highly undesirable and potentially explosive polynitrated hydrocarbons.

Nitration of hydrocarbons without the use of a mixture of nitric and sulfuric acids has also been described. Illustratively, U.S. Pat. No. 1,325,168 describes passing an oxidizing agent (oxygen) into a mixture of an aromatic hydrocarbon and liquid nitrogen peroxide. U.S. Pat. No. 2,109,873 describes passing a gaseous mixture of an aromatic hydrocarbon and nitrogen dioxide through a bed of silica gel to obtain the mononitro derivative of the aromatic hydrocarbon in low yield. U.S. Pat. No. 2,206,813 describes nitrating aliphatic hydrocarbons in the vapor phase using nitrogen dioxide at temperatures from 300° C to 600° C. U.S. Pat. No. 3,922,315 describes contacting nitrogen dioxide with a liquid phase mixture of an aromatic hydrocarbon and a rhodium catalyst in the presence of hydrogen, U.S. Pat. No. 3,869,253 teaches the nitration of saturated aliphatic hydrocarbons by reaction of the latter with nitrogen peroxide in the presence of oxygen under pressure.

It is an object of the present invention to provide a process which does not require the use of large volumes of a mixture of nitric and sulfuric acids or the use of relatively expensive heavy metal catalysts. It is also an object of the invention to provide a process which is highly selective and gives rise to substantially quantitative yields of the desired nitro compounds with no significant production of by-products, particularly those which are potentially explosive. It is a further object of the invention to provide a process which is readily adaptable to semicontinuous operation. These objects are achieved by the process which is described hereafter.

SUMMARY OF THE INVENTION

This invention comprises an improved process for the nitration of an aromatic hydrocarbon wherein the improvement comprises reacting said aromatic hydrocarbon with gaseous nitrogen dioxide in the presence of a catalytic amount of sulfuric acid and in the absence of oxygen at a temperature of about 50° C to about 150° C.

The invention also comprises a semi-continuous method of carrying out the above procedure in which the sulfuric acid employed as catalyst is recovered and re-used in a subsequent run of the process.

DETAILED DESCRIPTION OF THE INVENTION

The commonly used method of nitration of benzene, toluene, and the like aromatic hydrocarbons involves the use of a mixture of concentrated nitric and sulfuric acids, a mixture which is highly corrosive and very difficult to handle. Further, the amount of sulfuric acid employed in the mixture is usually well in excess of 1 mole per mole of aromatic hydrocarbon to be nitrated. We have found that the use of the mixed acids and the use of such large proportions can be avoided and, surprisingly, the overall result of the nitration process can be greatly improved by the process of this present invention.

Thus, we have found that the nitration of an aromatic hydrocarbon can be accomplished readily and in high yield by bringing a gaseous mixture of nitrogen dioxide, or its dimeric equivalent dinitrogen tetraoxide ($N_2O_4$), into contact with the aromatic hydrocarbon in the presence of a catalytic quantity of concentrated sulfuric acid and in the substantial absence of oxygen. The various reactants can be brought together in a variety of ways.

Illustratively, in a batch process the reaction is effected conveniently by bubbling a mixture of nitrogen dioxide and an inert gas such as nitrogen, carbon dioxide, argon, helium and the like, through a mixture of aromatic hydrocarbon and concentrated sulfuric acid housed in a suitable vessel. Any oxygen initially present in the reaction vessel is first displaced using inert gas prior to introduction of the nitrogen dioxide. In a continuous process the mixture of aromatic hydrocarbon and concentrated sulfuric acid can be allowed to flow down a packed column countercurrently to a mixture of nitrogen dioxide and inert gas which is passed upwardly through the column. If desired, a series or bank or such columns can be employed, the liquid product collected at the bottom of a column being passed as feed to the top of the next succeeding column and the gaseous effluent from the top of one column being passed to the bottom of the next preceding column, the flow of liquid and gas being in opposite directions throughout the series.

Other methods of carrying out the process of the invention will be apparent to one skilled in the art. In all the various procedures the amount of concentrated sulfuric acid employed is always catalytic, i.e. there is less than 1 mole of concentrated sulfuric acid per mole of aromatic hydrocarbon. Advantageously, the amount of concentrated sulfuric acid employed is within the range of about 0.1 mole to about 0.9 mole per mole of aromatic hydrocarbon and is preferably within the range of about 0.1 mole to about 0.3 mole per mole of aromatic hydrocarbon. The sulfuric acid is advantageously used in the form of concentrated sulfuric acid containing at least 30 percent by weight of $H_2SO_4$ and preferably 60 percent to 98 percent by weight of $H_2SO_4$.

The proportion of nitrogen dioxide employed in the process of the invention is advantageously at least 2 moles per mole of aromatic hydrocarbon for each nitro group which is to be introduced into the latter. Preferably the proportion of nitrogen dioxide is within the range of about 2 mole to about 3 per mole of aromatic hydrocarbon for each nitro group which is to be introduced into the latter.

The nitrogen dioxide and the inert gas can be introduced to the reaction site as separate streams or can be preblended and introduced as a single stream. As discussed above, the two gases and the aromatic hydrocarbon can be brought together in various different ways. Whichever procedure is employed the mixture of aromatic hydrocarbon and sulfuric acid catalyst is advantageously maintained at a temperature within the range of 50° C to 150° C and preferably within the range of 70° C to 100° C while the nitrogen dioxide and inert gas are introduced.

Where more than one nitro group is to be introduced into the aromatic hydrocarbon, the introduction of the first nitro group is often possible, and more convenient, at a temperature within the lower end of the above range. The introduction of the second, and any subsequent, nitro group is then conducted at a temperature in the higher end of the above range. Illustratively, toluene can be converted to mono-nitro-toluene at a temperature in the range of 50° C to 80° C and the mono-nitrotoluene can be nitrated further at a temperature in the range of 80° C to 150° C.

The process of the reaction can be followed by routine analytical procedures such as by nuclear magnetic resonance spectra and the like. When the desired endpoint has been reached, the nitrated aromatic hydrocarbon is isolated by any conventional procedure. Advantageously, in those cases where the product is sufficiently volatile, it is isolated by distillation leaving a residue of the sulfuric acid which has been used as catalyst. The distillation will generally remove some or most of the water of condensation which has been generated during the nitration process.

In any event, the recovered sulfuric acid can be treated, if necessary, to remove the water of condensation before being re-used in a subsequent nitration. This removal of water can be accomplished by azeotropic distillation using benzene. In the case where benzene is the aromatic hydrocarbon which is to be nitrated, the removal of water from recovered acid by azeotropic distillation forms a very convenient first step in process of the invention. Indeed, where benzene is the aromatic hydrocarbon which is being nitrated, it is also possible to remove water azeotropically from the reaction mixture as it is formed by suitble arrangement of reaction conditions, e.g. by collecting the azeotrope of benzene and water in a suitable trap, separating the benzene from the water and returning the benzene to the reaction mixture.

The process of the invention can be carried out in the presence of an inert organic solvent, if desired, although the use of such a solvent is not necessary in the case of those aromatic hydrocarbons which are liquid and which give rise to nitro derivatives which also are liquid at the reaction temperature employed. Illustrative of inert organic solvents, i.e. solvents which do not enter into reaction with any of the reaction components or interfere in any other way with the desired course of the reaction, are chloroform, ethylene dichloride, tetrachloroethane, carbon tetrachloride, nitromethane, acetonitrile and the like.

The process of the invention represents a marked improvement over nitration processes conventionally employed in the art. As set forth above, it avoids the use of the mixture of concentrated nitric and sulfuric acids hitherto employed, drastically reduces the amount of concentrated sulfuric acid employed and markedly increases the selectivity of the nitration. Thus, in the case of the nitration of benzene, the process of the invention will yield mono-nitrobenzene not contaminated with any significant quantitites of impurities, particularly the undesirable and potentially explosive polynitrated derivatives. Similarly, in the case of toluene, it is possible to produce mono-nitrotoluene substantially free from undesirable polynitro compounds and to subject this mono-nitro compound to further nitration to yield the dinitrotoluenes in a ratio of 2,4- to 2,6-dinitrotoluene pf about 80:20, without any substantial amount of by-product. The dinitrotoluenes so obtained are valuable intermediates in the preparation of the corresponding diamines and diisocyanates.

It is to be noted that, unless the process of the invention is carried out in the substantial absence of oxygen, the presence of undesirable by-products (mainly polynitro compounds) is detected in significant quantities (up to 2 percent by weight of product or higher). Thus, it is a critical requirement that all oxygen, i.e. air be displaced from the reaction mixture prior to introduction of the nitrogen dioxide and that the reaction be conducted in an inert atmosphere, i.e. an atmosphere substantially devoid of any oxygen.

The following examples describe the manner and process of making and using the invention and set forth the best mode contemplated by the inventors of carrying out the invention but are not to be construed as limiting.

EXAMPLE 1

A mixture of 156 g. (2 mole) of anhydrous benzene and 16 g. (0.14 mole) of 85.8 percent sulfuric acid was charged to a 250 ml. 4-necked round bottom flask equipped with gas inlet, stirrer, condenser, and thermometer. The mixture was purged with nitrogen and stirred at 70 ± 3° C while a mixture of nitrogen dioxide (flow rate circa 70 ml. per minute) and nitrogen (flow rate circa 130 ml. per minute) was bubbled into the solution through the gas inlet. The reaction was continued at the above temperature with continuous passage of the mixture of nitrogen dioxide and nitrogen at the above rate for a total of 4 hours. At the end of this time the reaction mixture was cooled to circa 20° C and the brown to red upper layer was separated, washed with 15 ml. of saturated sodium chloride solution and dried over anhydrous magnesium sulfate. The dried product was distilled to yield 91.39 g. of recovered benzene, 101.5 g. of nitrobenzene and 0.25 g. residue. The selectivity to nitrobenzene was 99.8 percent.

EXAMPLE 2

A mixture of 156 g. (2 mole) of anhydrous benzene and 38 g. (0.3 mole) of 77.4 percent sulfuric acid was charged to a 500 ml. flask, equipped as described in Example 1, purged with nitrogen and heated at 72 ± 3° C. A gaseous mixture of nitrogen (flow rate circa 70 ml./min.) and nitrogen dioxide (flow rate circa 130 ml./min.) [flow meter calibrated using air] was bubbled into the reaction mixture over a period of 8 hours while maintaining the reaction mixture in the above temperature range. At the end of this period the reaction mixture was cooled to 20° C and the upper layer was separated, washed with 15 ml. of saturated aqueous sodium chloride solution and dried over anhydrous magnesium sulfate. The dried solution was distilled to yield 6.5 g. of unreacted benzene, 228.7 g. of nitrobenzene (97 percent yield based on consumed benzene) and 0.66 g. residue.

The selectivity of conversion to nitrobenzene was 99.7 percent.

EXAMPLE 3

A mixture of 18.4 g. (0.2 mole) of dry toluene in 15 ml. of ethylene chloride as solvent and 3.75 g. (0.03 mole) of 78.4 percent sulfuric acid was charged to a 100 ml. flask equipped as described in Example 1. The mixture was purged with nitrogen and heated to 70° C. A gaseous mixture of nitrogen dioxide (flow rate circa 70 ml./min. flow meter calibrated using air) and nitrogen (flow rate circa 70 ml./min.) was then bubbled into the reaction mixture. The temperature was maintained at 70°–80° C over a period of 5 hours. At the end of this period the toluene in upper layer was shown by nuclear magnetic resonance (NMR) spectroscopy to be essentially completely mononitrated. The isomer ratio of ortho-, meta- and para-mononitrotoluene was 58.8:4.9:36.3, analyzed by vapor phase chromatography (VPC) using a 5% Carbowax column operated at 155° C. The mononitrated mixture, separated from the bottom aqueous acid layer, was diluted with another portion of 15 ml. ethylene chloride and charged, together with 11 g. (0.1 mole) of 89 percent sulfuric acid, to a 100 ml. flask equipped as previously described. The solution was treated with a gaseous mixture of nitrogen and nitrogen dioxide in the same manner as in the above-described mononitration at 80°–95° C. At the end of 15 hours, the product was found by NMR spectroscopy to consist essentially of dinitrotoluenes, mainly 2,4- and 2,6-dinitrotoluenes (ratio circa 78:22). Other isomers constituted approximately 2% of the total dinitrotoluenes. The conversion, judged by NMR and VPC, was greater than 95%.

We claim:

1. In a process for the nitration of an aromatic hydrocarbon the improvement which comprises reacting said hydrocarbon with gaseous nitrogen dioxide in the presence of a catalytic amount of sulfuric acid and in the substantial absence of oxygen at a temperature of about 50° C to about 150° C.

2. The process of claim 1 wherein the amount of nitrogen dioxide employed is at least two moles per mole of aromatic hydrocarbon.

3. The process of claim 1 wherein a gaseous mixture of nitrogen dioxide and an inert gas is passed into a liquid mixture of said aromatic hydrocarbon and said sulfuric acid.

4. A process according to claim 1 wherein, at the end of the nitration process, the nitro-substituted aromatic hydrocarbon is removed by distillation and the residual sulfuric acid is re-used as the catalyst in the subsequent nitration.

5. The process of claim 1 wherein the aromatic hydrocarbon is benzene.

6. The process of claim 1 wherein the aromatic hydrocarbon is toluene.

7. A process for the preparation of nitrobenzene substantially free from polynitrated by-products which comprises reacting benzene with gaseous nitrogen dioxide at a temperature of 50° C to 150° C in the presence of a catalytic amount of sulfuric acid and in the substantial absence of oxygen.

8. The process of claim 7 werein the amount of nitrogen dioxide employed is at least two moles per mole of benzene.

9. The process of claim 7 wherein the amount of nitrogen dioxide employed is about 2 to about 3 moles per mole of benzene.

10. A process for the preparation of a mixture of mononitrotoluenes substantially free from more highly nitrated by-products which comprises reacting toluene with gaseous nitrogen dioxide at a temperature of 50° C to 150° C in the presence of a catalytic amount of sulfuric acid and in the substantial absence of oxygen.

11. The process of claim 10 wherein the amount of nitrogen dioxide employed is at least 2 moles per mole of toluene.

12. The process of claim 10 wherein the mixture of mononitrotoluene is further reacted with at least 2 moles, per mole of mononitrotoluene, of gaseous nitrogen dioxide at a temperature of 50° C to 150° C in the presence of a catalytic amount of sulfuric acid and in the substantial absence of oxygen to obtain a mixture of dinitrotoluenes substantially free from more highly nitrated by-products.

* * * * *

UNITED STATES PATENT OFFICE
CERTIFICATE OF CORRECTION

Patent No. 4,123,466                Dated October 31, 1978

Inventor(s) Chung-Yuan Lin, Fred A. Stuber and Henri Ulrich

It is certified that error appears in the above-identified patent and that said Letters Patent are hereby corrected as shown below:

Column 2, line 39:           Should read:

bank or                      bank of

Column 3, line 23:           Should read:

process                      progress

Column 3, line 45:           Should read:

suitble                      suitable

Column 3, line 55:           Should read:

temperature                  temperatures

Column 4, lines 9 and 10:    Should read:

pf about                     of about

UNITED STATES PATENT OFFICE
CERTIFICATE OF CORRECTION

Patent No. 4,123,466         Dated October 31, 1978

Inventor(s) Chung-Yuan Lin, Fred A. Stuber and Henri Ulrich

It is certified that error appears in the above-identified patent and that said Letters Patent are hereby corrected as shown below:

Column 6, claim 4, line 11:          Should read:

in the subsequent                     in a subsequent

Column 6, claim 8, line 23:          Should read:

werein                                wherein

Column 6, claim 12, line 39:         Should read:

mononitrotoluene                      mononitrotoluenes

Signed and Sealed this

Fifteenth Day of May 1979

[SEAL]

Attest:

RUTH C. MASON
Attesting Officer

DONALD W. BANNER
Commissioner of Patents and Trademarks